(12) United States Patent
Jin

(10) Patent No.: US 8,927,735 B2
(45) Date of Patent: Jan. 6, 2015

(54) PREPARATION OF N-SUBSTITUTED ISOTHIAZOLINONE DERIVATIVES

(75) Inventor: Yuechun Jin, Beijing (CN)

(73) Assignee: Beijing Tianqing Chemicals Co. Ltd., Beijing (CN)

( * ) Notice: Subject to any disclaimer, the term of this patent is extended or adjusted under 35 U.S.C. 154(b) by 983 days.

(21) Appl. No.: 13/008,344

(22) Filed: Jan. 18, 2011

(65) Prior Publication Data

US 2011/0112327 A1    May 12, 2011

Related U.S. Application Data

(62) Division of application No. 11/997,963, filed as application No. PCT/CN2006/000590 on Apr. 3, 2006, now Pat. No. 7,893,273.

(51) Int. Cl.
*C07D 275/02* (2006.01)
*C07D 275/03* (2006.01)

(52) U.S. Cl.
CPC ............ *C07D 275/03* (2013.01); *C07D 323/60* (2013.01)
USPC .......................................... 548/213; 548/206

(58) Field of Classification Search
CPC ...................................................... C07D 275/02
USPC ................................... 548/206, 213
See application file for complete search history.

(56) References Cited

U.S. PATENT DOCUMENTS

| | | | |
|---|---|---|---|
| 3,849,430 A | 11/1974 | Lewis et al. | |
| 4,105,431 A | 8/1978 | Lewis et al. | |
| 4,783,221 A | 11/1988 | Grove et al. | |
| 5,315,008 A | 5/1994 | Effenberger et al. | |
| 5,420,290 A * | 5/1995 | Bayer et al. | 548/213 |
| 5,453,507 A | 9/1995 | Hahn et al. | |
| 5,919,400 A * | 7/1999 | Kim et al. | 252/405 |
| 6,376,680 B1 | 4/2002 | Kim et al. | |
| 6,479,701 B1 | 11/2002 | Kim et al. | |
| 6,506,904 B1 | 1/2003 | Kim et al. | |
| 7,442,240 B2 | 10/2008 | Yu et al. | |
| 7,983,273 B2 * | 7/2011 | Beshai | 370/395.4 |

FOREIGN PATENT DOCUMENTS

| | | |
|---|---|---|
| CA | 2021669 A1 | 1/1991 |
| CN | 1629148 A | 6/2005 |
| CN | 1634899 A | 7/2005 |
| CN | 1233635 C | 12/2005 |
| EP | 0 095 907 A2 | 12/1983 |
| EP | 0 375 265 A | 6/1990 |
| EP | 0 648 757 A1 | 4/1995 |
| EP | 1113012 A1 | 7/2001 |
| JP | 03-81259 A | 5/1991 |
| JP | 03-128368 A | 5/1991 |
| JP | 03-236380 A | 10/1991 |
| JP | 06-507609 A | 9/1994 |
| JP | 07-101948 A | 4/1995 |
| JP | 2001-181266 A | 7/2001 |
| JP | 2003-335763 A | 11/2003 |
| WO | WO 92/20664 A1 | 11/1992 |

OTHER PUBLICATIONS

Wang et al (2006): STN International HCAPLUS database, (Columbus, Ohio), Accession No. 2008:133160.*
Wang et al (1993): Huaxue Shiji, vol. 15 (1), p. 60, 1993.*
Khalaj et al.; "Synthesis and antibacterial activity of 2-(4-substituted phenyl)-3(2H)-isothialozones"; *Eur. J. Med. Chem.*; 36:699-705 (2004).
Kim et al.; STN International HCAPLUS database (Columbus, OH); Accession No. 2002:312039 (2002).

* cited by examiner

*Primary Examiner* — Golam M M Shameem
(74) *Attorney, Agent, or Firm* — Kilpatrick Townsend & Stockton LLP

(57) ABSTRACT

Provided is a process for the preparation of an N-substituted isothiazolinone derivative having the general formula (I), comprising reacting N-substituted 3-mercaptopropionamides of formula (II) or N,N'-bis-substituted 3,3'-dithiodipropionamides of formula (III) with sulfuryl chloride in the absence of solvents. Also provided is a process for the preparation of a compound having the general formula (III), comprising reacting a methyl ester of formula (IV) with an amine of formula (V) in a solvent of methanol. As no addition solvent is used in the process of the invention, the cost of manufacturing and pollution to the environment can be reduced.

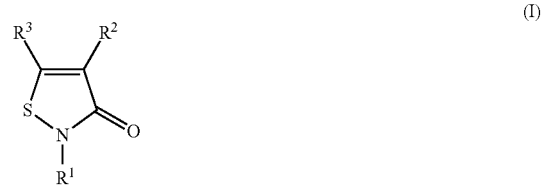

(I)

7 Claims, No Drawings

PREPARATION OF N-SUBSTITUTED ISOTHIAZOLINONE DERIVATIVES

RELATED APPLICATIONS

This application is a divisional of U.S. patent application Ser. No. 11/997,963, filed Feb. 5, 2008, now U.S. Pat. No. 7,893,273, which is a National Stage Entry of International Patent Application No. PCT/CN2006/000590, filed Apr. 3, 2006, the contents of all of the above are incorporated by reference in the entirety.

FIELD OF THE INVENTION

The present invention relates to the preparation of isothiazolinone derivatives, and more specifically, to the preparation of N-substituted isothiazolinone derivatives.

BACKGROUND OF THE INVENTION

Isothiazolinone compounds are a novel kind of potent and broad-spectrum antiseptics possessing the advantages of high potency, low toxicity, a long effective period and harmlessness to the environment over conventional antiseptics. Therefore, isothiazolinone compounds have broad applications in the fields of water treatment, cosmetics, construction materials, binding agents, paints, medical treatment, fabrics, photographs and detergents, and especially can be used as antifouling agents in marine antifouling coatings.

Till now, a number of methods for preparing N-substituted isothiazolinone derivatives have been reported, most of which comprise the step of reacting a N,N'-bis-substituted dithiodipropionamide or a N-substituted mercaptopropionamide with a halogenating agent in an organic solvent.

For example, Chinese Patent Applications CN1634889 and CN1629148 disclose, respectively, processes for preparing N-alkoxy propylisothiazolinones and N-alkoxyethoxy propylisothiazolinones, which comprise reacting the corresponding N,N'-bis-substituted dithiodipropionamides with sulfuryl chloride in ethyl acetate.

Japanese Patent Application JP2003-335763 discloses a process for the preparation of 2-substituted-4-isothiazolin-3-ones, which comprises reacting N-substituted mercaptopropionamides or N,N'-bis-substituted dithiodipropionamides with a halogenating agent in ethyl acetate.

European Patent Application EP0498347 discloses a process for the preparation of 2-methyl-isothiazolin-3-ones, which comprises reacting N-methyl-3-mecaptopropionamides with chlorine in a solvent of aromatic or halogenated hydrocarbon, such as benzene, toluene, chlorobenzene, chloroform and the like.

European Patent Application EP1113012 discloses a process for the preparation of 2-alkyl-4-isothiazolin-3-ones, which comprises reacting N-alkyl mecaptopropionamides or N,N'-dialkyl dithiodipropionamides with a chlorinating agent in a solvent, in which hydrogen chloride is insoluble or has low solubility, such as halogenated aliphatic hydrocarbons, halogenated aromatic hydrocarbons or aliphatic hydrocarbons.

U.S. Pat. No. 5,453,507 discloses a process for the preparation of N,N'-dimethyl or N,N'-di-n-octyl-4-isothiazolin-3-ones, which comprises reacting N,N'-bis-substituted dithiodipropionamides with sulfuryl chloride in a halogenated organic solvent, such as $CH_2X_2$, $CHX_3$, $CX_3CH_3$ and $CHX_2CHX_2$.

However, the use of organic solvents in the processes of the prior art causes a lot of problems. For example, firstly the use of the solvent will decrease the volumetric efficiency of the reactor thereby decreasing the productivity; secondly the post-treatment and recovery of the solvent will increase the operation cost; thirdly the solvent will bring impurities into the reaction system thereby complicating the separation and purification of the desired products; and lastly the organic solvent used, especially benzene and halogenated hydrocarbons, generally has an adverse effect on the environment.

SUMMARY OF THE INVENTION

The present invention aims at providing an improved process for the preparation of N-substituted isothiazolinone derivatives, which is more cost-effective and less harmful to the environment.

According to an aspect of the invention, there is provided a process for the preparation of a compound having the following general formula (I),

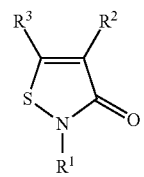
(I)

in which
$R^1$ is selected from the group consisting of alkyl, cycloalkyl and aryl, optionally substituted by a substituent selected from the group consisting of alkyl, aryl, alkoxy and aryloxy; and
$R^2$ and $R^3$, each independently, represent hydrogen or chlorine, comprising:
reacting a compound having the following general formula (II),

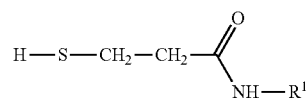
(II)

in which $R^1$ is as previously defined,
or a compound having the following general formula (III),

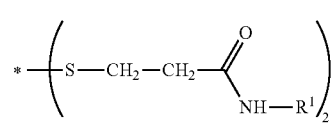
(III)

in which $R^1$ is as previously defined,
with sulfuryl chloride in the absence of a solvent.

According a preferred embodiment of the invention, $R^1$ is selected from the group consisting of $C_1$-$C_8$ alkyl, $C_3$-$C_8$ cycloalkyl and $C_6$-$C_{10}$ aryl, optionally substituted by a substituent selected from the group consisting of $C_1$-$C_8$ alkyl, $C_6$-$C_{10}$ aryl, $C_1$-$C_8$ alkoxy and $C_6$-$C_{10}$ aryloxy. More preferably, $R^1$ represents $C_1$-$C_8$ alkyl optionally substituted by $C_6$-$C_{10}$ aryl or $C_1$-$C_8$ alkoxy.

According to another preferred embodiment of the invention, $R^2$ and $R^3$ both represent hydrogen or chlorine.

Preferably, the reaction is carried out at a temperature between about −10° C. and about 75° C., and more preferably between room temperature and about 45° C.

According to the process of the invention, N-substituted isothiazolinone derivatives can be prepared in the absence of a solvent, and therefore problems caused by using an organic solvent in the prior art can be avoided, and the cost of manufacturing and pollution to the environment can be greatly reduced.

According to another aspect of the invention, there is provided a process for the preparation of a compound having the following general formula (III), comprising the step of reacting a compound having formula (IV),

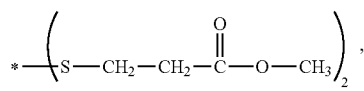  (IV)

with a compound having the general formula (V), $H_2N-R^1$  (V)

in which $R^1$ is as previously defined, in a solvent of methanol.

According to a preferred embodiment of this process in the invention, the molar ratio of the compound of formula (IV) to the compound of formula (V) is between about 1:2.0 and 1:2.6. The temperature of the reaction is preferably between about −15° C. and about 65° C.

According to the process of the invention, no further impurities will be generated into the reaction system during the preparation of the compound of formula (III), and the separation and purification thereof can be greatly simplified in comparison with processes in the prior art.

DETAILED DESCRIPTION OF THE INVENTION

As described above, in an aspect of the invention, there is provided a process for the preparation of an N-substituted isothiazolinone derivative having the following general formula (I),

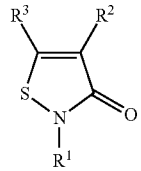  (I)

in which $R^1$ is selected from the group consisting of alkyl, cycloalkyl and aryl, optionally substituted by a substituent selected from the group consisting of alkyl, aryl, alkoxy and aryloxy; and $R^2$ and $R^3$, each independently, represent hydrogen or chlorine, comprising the step of reacting an N-substituted 3-mercaptopropionamide having the following general formula (II),

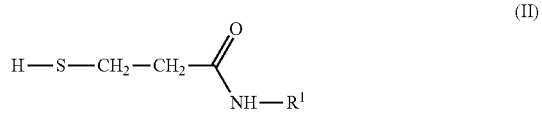  (II)

in which $R^1$ is as previously defined, or an N,N'-bis-substituted 3,3'-dithiodipropionamide having the following general formula (III),

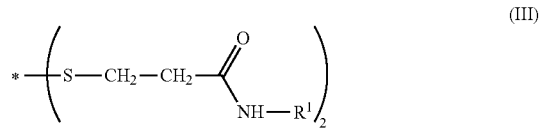  (III)

in which $R^1$ is as previously defined, with sulfuryl chloride in the absence of a solvent.

The term "alkyl", as used herein, generally refers to a straight or branched saturated aliphatic hydrocarbon group, preferably $C_1$-$C_{10}$ alkyl, and more preferably $C_1$-$C_8$ alkyl, such as methyl, ethyl, n-propyl, isopropyl, n-butyl, isobutyl, tert-butyl, n-pentyl, n-hexyl, n-heptyl, n-octyl and the like.

The term "cycloalkyl", as used herein, generally refers to a saturated alicyclic hydrocarbon group, preferably $C_3$-$C_{10}$ cycloalkyl, and more preferably $C_3$-$C_8$ cycloalkyl, such as cyclopropyl, cyclobutyl, cyclopentyl and the like.

The term "aryl", as used herein, generally refers to an aromatic hydrocarbon group, preferably $C_6$-$C_{20}$ aryl, more preferably $C_6$-$C_{10}$ aryl, such as phenyl and naphthyl, and most preferably phenyl.

The term "in absence of a solvent", as used herein, means that, except the reactants themselves, no other substances are added to the reaction system to dissolve the reactants, intermediates or products.

During the preparation of isothiazolinone derivatives according to the process of the invention, sulfuryl chloride in the reaction system acts as both the reactant and the solvent at the beginning of the reaction; and after sulfuryl chloride is depleted, the resultant isothiazolinone derivative acts as a solvent, and therefore no addition solvent is needed.

In particular embodiments of the invention, the desired product can be separated using well-known techniques including, but not limited to, recrystallization and solvent extraction.

In a preferred embodiment of the invention, $R^1$ represents $C_1$-$C_8$ alkyl optionally substituted by $C_6$-$C_{10}$ aryl or $C_1$-$C_8$ alkoxy. More preferably, $R^1$ represents $C_1$-$C_8$ alkyl, especially n-octyl.

In another preferred embodiment of the invention, $R^2$ and $R^3$ both represent hydrogen or chlorine.

In some preferred embodiments, the process of the invention comprises reacting a compound of formula (II) with sulfuryl chloride. More preferably, the molar ratio of the compound of formula (II) to sulfuryl chloride is between about 1:1 and 1:11.

In other embodiments of the invention, chlorine can be used in addition to surfuryl chloride as a chlorinating agent.

In a preferred embodiment, the process of the invention comprises reacting a compound of formula (III) with sulfuryl chloride optionally in the presence of chlorine. More preferably, the molar ratio between the compound of formula (III), sulfuryl chloride and chlorine is about 1:1-11:0-11, and further more preferably about 1:1-3:5-7.

In a particularly preferred embodiment, the process of the invention further comprises the step of preparing a compound of formula (III), which comprises reacting dimethyl 3,3'-dithiodipropionate of formula (IV),

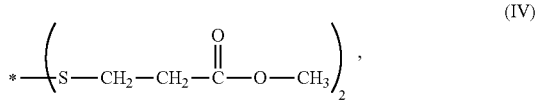

with an amine having the general formula (V), $$H_2N—R^1 \qquad (V)$$

in which $R^1$ is as previously defined,
in a solvent of methanol.

More preferably, the molar ratio of the compound of formula (IV) to the compound of formula (V) is between about 1:2.0 and 1:2.6. The temperature of the reaction between the compound of formula (IV) and the compound of formula (V) is preferably between about −15° C. and about 65° C., and more preferably between about 5° C. and room temperature. The reaction time is about 3 hours to 5 days.

In another aspect of the invention, there is provided a process for the preparation of a compound of formula (III), comprising reacting dimethyl 3,3'-dithiodipropionate of formula (IV),

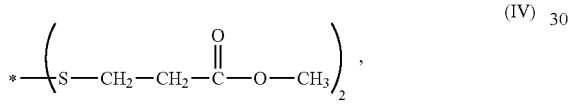

with an amine having the general formula (V), $$H_2N—R^1 \qquad (V)$$

in which $R^1$ is as previously defined,
in a solvent of methanol.

Preferably, $R^1$ represents $C_1$-$C_8$ alkyl optionally substituted by $C_6$-$C_{10}$ aryl or $C_1$-$C_8$ alkoxy. More preferably, $R^1$ represents $C_1$-$C_8$ alkyl, especially n-octyl.

And preferably, the molar ratio of the compound of formula (IV) to the compound of formula (V) is between about 1:2.0 and 1:2.6. The reaction temperature is preferably between about −15° C. and about 65° C., and more preferably between about 5° C. and room temperature. The reaction time is about 3 hours to 5 days.

As methanol is a product of the reaction between the compound of formula (IV) and the compound of formula (V), use of methanol as a solvent in the process of the invention would not introduce into the reaction system any undesired impurity. Thus, the separation and purification of the desired product can be greatly simplified. More specifically, in comparison with processes where water is used as a solvent, the product obtained according to the process of the invention has a greater particle size and therefore can be easily separated from the mother liquor. And according to the process of the invention, the remaining mother liquor can be recycled and methanol can be recovered by evaporation. As a result, waste emission to the environment is greatly reduced.

EXAMPLES

Hereinafter, preferred embodiments of the invention will be illustrated in detail with reference to the following examples, which should be considered only illustrative and non-limitative.

Example 1

Preparation of N,N'-di-n-octyl-3,3'-dithiodipropionamide

The reaction scheme is as follows:

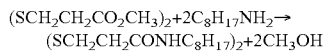

238 g (1 mol) of dimethyl 3,3'-dithiodipropionamide and 280 g (2.17 mol) of n-octylamine were added into 300 ml of methanol in a 1,000 ml reaction flask, and the reactants stirred at 5° C. for 5 days (under nitrogen atmosphere, if desired). The reaction mixture was then cooled to −10° C., and separated by centrifuging to give 329 g of a solid of N,N'-di-n-octyl-3,3'-dithiodipropionamide (purity >95%, yield 76%). The mother liquor was recycled after methanol was recovered by evaporation.

Example 2

Preparation of N-n-octyl isothiazolinones (including N-n-octyl-4-isothiazolin-3-one (OIT) and N-n-octyl-4,5-dichloro-4-isothiazolin-3-one (DCOIT))

The reaction scheme is as follows:

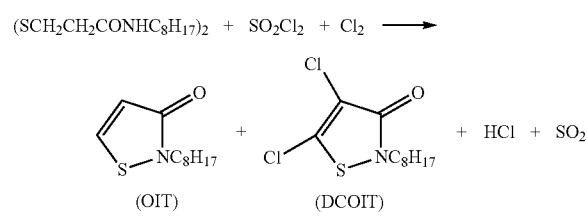

200 ml (330 g, 2.44 mol) of sulfuryl chloride was added into a 1,000 ml reaction flask, to which 648 g (1.5 mol) of N,N'-di-n-octyl-3,3'-dithiodipropionamide was then added for 6.5 hours (about 100 g per hour) under agitation. After 3 hours of reaction, chlorine was aerated into the reaction mixture at about 50 g per hour for 13 hours (about 650 g in total, 9.15 mol). When the temperature of the reaction mixture reached 40° C., the mixture was cooled with saline and maintained at a temperature of 40-45° C. After the aeration of chlorine was completed, the reaction mixture was stirred at the same temperature for 2 hours.

The reaction mixture was washed with hot water at 50° C. in another 1,000 ml reaction flask till it became weakly acidic, and, if desired, sodium bicarbonate was used to neutralize excessive acid. The precipitate was recrystallized in methanol to give 190 g of DCOIT (purity >95%). The recrystallization mother liquor was then extracted successively with petroleum ether and methanol to afford 61 g of OIT (purity >93%, yield 19%) and 49 g of DCOIT (purity >95%). The total yield of DCOIT is 56.5%.

It should be understood that although the present invention has been specifically disclosed by the preferred embodiments and examples, modifications and variations thereto, without departing from the spirit of the invention, may be pursued by those skilled in the art, and such modifications and variations should fall within the scope of the invention.

The invention claimed is:

1. A process for the preparation of a compound of formula (III),

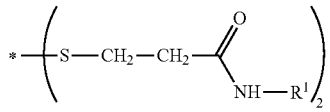
(III)

wherein
R¹ is selected from the group consisting of $C_1$-$C_8$ alkyl, $C_3$-$C_8$ cycloalkyl and $C_6$-$C_{10}$ aryl, optionally substituted by a substituent selected from the group consisting of $C_1$-$C_8$ alkyl, $C_6$-$C_{10}$ aryl, $C_1$-$C_8$ alkoxy and $C_6$-$C_{10}$ aryloxy,
the process comprising reacting, in a solvent of methanol, a compound of formula (IV),

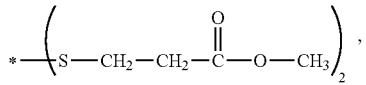
(IV)

with a compound having formula (V),

(V)

2. The process according to claim 1, wherein the molar ratio of the compound of formula (IV) to the compound of formula (V) is between about 1:2.0 and 1:2.6.

3. The process according to claim 1 or 2, wherein the reaction between the compound of formula (IV) and the compound of formula (V) is carried out at a temperature between about −15° C. and about 65° C.

4. The process according to claim 1, wherein R¹ is $C_1$-$C_8$ alkyl.

5. The process according to claim 1, wherein R¹ is n-octyl.

6. The process according to claim 1, wherein the reaction between the compound of formula (IV) and the compound of formula (V) is carried out at a temperature between about 5° C. and room temperature.

7. The process according to claim 1, wherein the reaction between the compound of formula (IV) and the compound of formula (V) is carried out for about 3 hours to 5 days.

* * * * *